United States Patent [19]

Kordes

[11] Patent Number: Plant 6,513

[45] Date of Patent: Jan. 3, 1989

[54] ROSE PLANT KORTEXUNG

[75] Inventor: Reimer Kordes, Klein Offenseth, Fed. Rep. of Germany

[73] Assignee: Jackson & Perkins Company, Medford, Oreg.

[21] Appl. No.: 27,619

[22] Filed: Mar. 18, 1987

[51] Int. Cl.[4] ..... A01H 5/00

[52] U.S. Cl. ..... Plt./26

[58] Field of Search ..... Plt./26

*Primary Examiner*—James R. Feyrer

*Attorney, Agent, or Firm*—Majestic, Gallagher, Parsons & Siebert

[57] ABSTRACT

A rose variety of the floribunda class is provided having an extremely long vase life for the buds and flowers, short to medium length cutting stems (less than twenty inches), high resistance to powdery mildew, and excellent flower production of long-lasting, light pink flowers.

1 Drawing Sheet

SUMMARY OF THE INVENTION

The present invention relates to a new and distinct variety of rose plant of the floribunda class, which was originated by me by crossing an unnamed seedling with an unnamed seedling.

The primary objective of this breeding was to produce a new rose variety of the floribunda class bearing flowers in the pink color range that are suitable for the production of cut blooms. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Light pink buds that are very slow opening;
2. Light pink flowers with extremely long vase life;
3. Strong color retention;
4. High flower production of short to medium length stems;
5. Resistance to powdery mildew;
6. Stiff petals.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Kortexung". Color terminology is in accordance with The Royal Horticultural Society Colour Chart except where an ordinary dictionary significance for the color is apparent.

Observations of the buds and flowers were made from specimens grown in a greenhouse at Irvine, Calif. in November through December.

Flower

The blooming habit is recurrent and continuous. The bud size is one to one and one-half inches when the petals start to unfurl. The bud form is long, pointed ovoid. The bud color when sepals first divide is near Red 49B to 49C; when half blown, the upper side of petals is near Red 49C and the lower side of petals is near Red 49C. The sepals have a color near Green 138B. The surface texture is smooth with some very fine hairs. There are three appendaged sepals lightly appendaged, and two unappendaged sepals with hairy edge. The receptacle color is near Green 138B of a funnel shape, small size and smooth surface. The peduncle is of medium length, smooth surface with some very fine hairs. Peduncle color is medium green, and the peduncle is stiff and erect.

Bloom

Bloom size is small, with an average open size of two and one-half to three inches, borne singly. The stems are strong, and medium to short. The form when first open is high center. This form is retained to the end. The outer petals curl back quill fashion. Under normal conditions there are thirty petals. The upper side of petal is near Red 49C, as is the reverse side of the petals. The base of petals is white semicircle near White 155B with the major color being near Red 49C. There are no variegations. The general tonality at the end of the first day shows no change in color. At the end of the third day, there remains no discoloration.

The fragrance is slight. The petal texture is thick, of a deltoid shape and the tips are slightly recurved and becoming quilled.

The arrangement is imbricated with no petaloids in the center. The blooms drop off cleanly, and last both on the plant and as a cut flower for a very long time.

Reproductive Parts

The anthers are medium size, of yellow color and arranged regularly around the styles. The pollen is pale yellow, and the styles and stigmas are white.

Plant

A very vigorous growth of bush form.

Foliage

Medium size, sparse in quantity. The new foliage is reddish, and the old foliage is dark green near Green 139A. Normal mid-stem leaves have five to seven leaflets.

The leaflets are of an oval pointed shape, are glossy, and have a smooth texture with a serrated edge. The serration is single and medium in size. Petiole rachis is green and petiole underside is smooth with few prickles. Stipules are short and bearded. The foliage is resistant to mildew under normal growing conditions at Irvine, Calif.

Wood

New wood is light green, with a smooth bark. Old wood is green with a smooth bark.

Prickles

There are few prickles on main canes from the base and few on laterals from the main canes. The form is medium and straight. Color when young is red.

Small Prickles

There are no small prickles on the main stalks or on the laterals.

Parentage

Both the seed parent and the pollen parent were unnamed seedlings.

Classification

Botanical is rosa hybrid. Commercial is floribunda.

I claim:

1. A new and distinct variety of rose plant and parts thereof of the floribunda class substantially as herein shown and described, characterized particularly as to novelty by the unique combination of its extremely long vase life, short to medium length cutting stems, high resistance to powdery mildew, excellent flower production, and long-lasting light pink color.

* * * * *

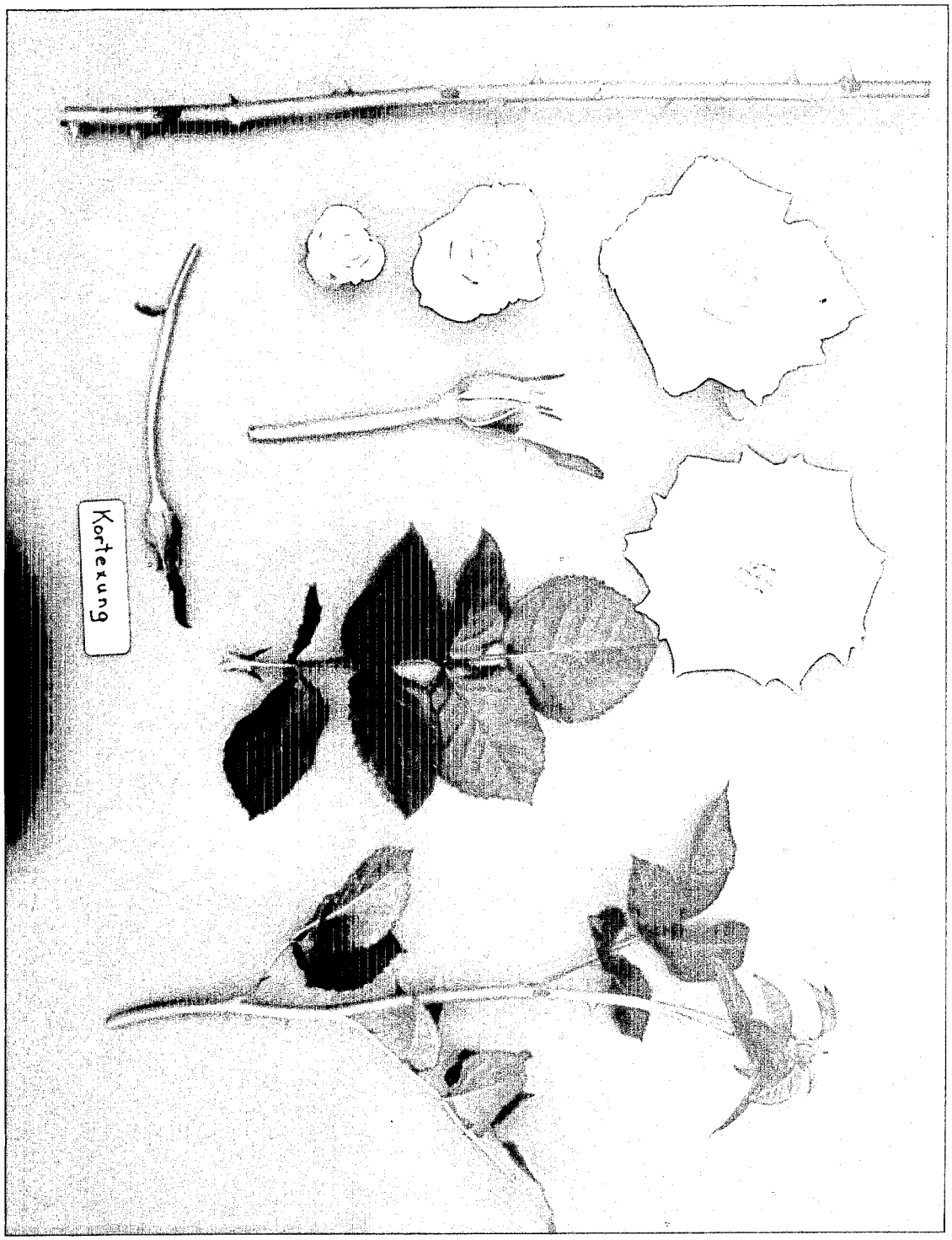
Kortexung